US007753960B2

(12) United States Patent
Cipolletti et al.

(10) Patent No.: US 7,753,960 B2
(45) Date of Patent: Jul. 13, 2010

(54) MODULAR KNEE PROSTHESIS

(75) Inventors: George Cipolletti, Duxbury, MA (US); Edward J. Cheal, Duxbury, MA (US); James H. Henry, Edmond, OK (US)

(73) Assignee: OMNI life science, Inc., East Taunton, MA (US)

( * ) Notice: Subject to any disclaimer, the term of this patent is extended or adjusted under 35 U.S.C. 154(b) by 840 days.

(21) Appl. No.: 11/066,123

(22) Filed: Feb. 25, 2005

(65) Prior Publication Data

US 2005/0203629 A1 Sep. 15, 2005

Related U.S. Application Data

(60) Provisional application No. 60/547,627, filed on Feb. 26, 2004.

(51) Int. Cl.
*A61F 2/38* (2006.01)

(52) U.S. Cl. .................................................. 623/20.29

(58) Field of Classification Search ... 623/20.14–20.36, 623/13.12–13.2, 39
See application file for complete search history.

(56) References Cited

U.S. PATENT DOCUMENTS 3,816,855 A * 6/1974 Saleh ...................... 623/20.31
3,868,730 A * 3/1975 Kaufer et al. ............ 623/20.22
3,869,729 A * 3/1975 Attenborough .......... 623/20.25
4,016,606 A * 4/1977 Murray et al. ........... 623/20.21
4,136,405 A * 1/1979 Pastrick et al. ........... 623/20.25
4,212,087 A 7/1980 Mortensen
4,213,209 A * 7/1980 Insall et al. .............. 623/20.27
4,216,549 A * 8/1980 Hillberry et al. ......... 623/20.26
4,219,893 A * 9/1980 Noiles ..................... 623/20.25
4,224,697 A * 9/1980 Murray et al. ........... 623/20.25
4,262,368 A * 4/1981 Lacey ...................... 623/20.25
4,268,920 A * 5/1981 Engelbrecht et al. ..... 623/20.26
4,301,553 A * 11/1981 Noiles ..................... 623/20.25
4,479,271 A * 10/1984 Bolesky et al. ........... 623/20.17
4,634,444 A * 1/1987 Noiles ..................... 623/20.27
4,731,086 A * 3/1988 Whiteside et al. ........ 623/20.16
4,822,366 A * 4/1989 Bolesky ................... 623/20.15
4,838,891 A * 6/1989 Branemark et al. ........ 623/20.3
4,865,606 A * 9/1989 Rehder .................... 623/20.23
4,888,021 A * 12/1989 Forte et al. ............... 623/20.19
4,936,847 A * 6/1990 Manginelli ............... 623/20.16
4,938,769 A * 7/1990 Shaw ...................... 623/20.15
4,944,756 A * 7/1990 Kenna ..................... 623/20.19
4,944,757 A * 7/1990 Martinez et al. ......... 623/20.15
4,950,298 A * 8/1990 Gustilo et al. ............ 623/20.15
4,995,883 A 2/1991 Demane et al.

(Continued)

FOREIGN PATENT DOCUMENTS

EP 0679375 A1 11/1995

(Continued)

*Primary Examiner*—David Isabella
*Assistant Examiner*—Ann Schillinger
(74) *Attorney, Agent, or Firm*—Scott E. Kamholz; Peter K. Sollins; Foley Hoag LLP

(57) ABSTRACT

A joint prosthesis may include a tibial tray, a tibial base, a tibial articular member, and a femoral articular member. In some embodiments, a coupler engages the tray, and optionally the base, with an interference fit. In some embodiments, the base engages the tray with an interference fit.

24 Claims, 6 Drawing Sheets

4
3
9
2
6
8
7
5
11
1
10

U.S. PATENT DOCUMENTS 5,002,578 A 3/1991 Luman
5,007,933 A * 4/1991 Sidebotham et al. ..... 623/20.27
5,030,234 A 7/1991 Pappas et al.
5,047,033 A 9/1991 Fallin
5,074,879 A 12/1991 Pappas et al.
5,080,674 A 1/1992 Jacobs et al.
5,108,452 A 4/1992 DeMane et al.
5,116,375 A * 5/1992 Hofmann ................ 623/20.27
5,147,405 A * 9/1992 Van Zile et al. .......... 623/20.27
5,147,406 A * 9/1992 Houston et al. .......... 623/20.15
5,163,961 A 11/1992 Harwin
5,194,066 A * 3/1993 Van Zile .................. 623/20.15
5,197,488 A * 3/1993 Kovacevic .................. 600/595
5,207,711 A * 5/1993 Caspari et al. ............ 623/20.3
5,236,461 A * 8/1993 Forte ...................... 623/20.27
5,246,459 A * 9/1993 Elias ...................... 623/20.34
5,271,747 A * 12/1993 Wagner et al. .......... 623/20.27
5,282,867 A * 2/1994 Mikhail .................. 623/13.12
5,314,481 A * 5/1994 Bianco .................. 623/20.25
5,330,534 A * 7/1994 Herrington et al. ....... 623/20.27
5,358,527 A * 10/1994 Forte ...................... 623/20.27
5,370,699 A * 12/1994 Hood et al. ............. 623/20.28
5,370,701 A * 12/1994 Finn ........................ 623/20.25
5,395,401 A * 3/1995 Bahler .................... 623/20.29
5,405,394 A 4/1995 Davidson
5,480,443 A * 1/1996 Elias ...................... 623/20.18
5,489,311 A * 2/1996 Cipolletti ................ 623/20.34
5,507,824 A 4/1996 Lennox
5,507,830 A 4/1996 DeMane et al.
5,514,183 A * 5/1996 Epstein et al. .......... 623/20.23
5,549,689 A * 8/1996 Epstein et al. .......... 623/20.23
5,556,433 A * 9/1996 Gabriel et al. .......... 623/20.36
5,601,567 A 2/1997 Swajger et al.
5,653,764 A 8/1997 Murphy
5,653,765 A 8/1997 McTighe et al.
5,658,341 A * 8/1997 Delfosse .................. 623/20.32
5,683,472 A * 11/1997 O'Neil et al. ........... 623/20.31
5,702,480 A 12/1997 Kropf et al.
5,755,804 A * 5/1998 Schmotzer et al. ....... 623/20.24
5,766,257 A * 6/1998 Goodman et al. ........ 623/20.21
5,782,921 A * 7/1998 Colleran et al. .......... 623/20.15
5,871,545 A * 2/1999 Goodfellow et al. ..... 623/20.28
5,876,459 A 3/1999 Powell
5,879,391 A * 3/1999 Slamin .................... 623/20.15
5,879,392 A * 3/1999 McMinn .................. 623/20.28
5,906,644 A 5/1999 Powell
5,941,911 A * 8/1999 Buechel ................... 623/11.11
5,954,770 A * 9/1999 Schmotzer et al. ....... 623/20.24
5,957,979 A 9/1999 Beckman et al.
5,964,808 A * 10/1999 Blaha et al. ............. 623/20.28
6,080,195 A * 6/2000 Colleran et al. .......... 623/20.32
6,099,569 A 8/2000 Keller
6,099,570 A * 8/2000 Livet et al. ............... 623/20.21
6,139,581 A * 10/2000 Engh et al. ............... 623/20.34
6,165,223 A * 12/2000 Metzger et al. .......... 623/20.27
6,203,576 B1 * 3/2001 Afriat et al. .............. 623/20.27
6,214,052 B1 * 4/2001 Burkinshaw ............. 623/20.34
6,238,436 B1 5/2001 Lob et al.
6,299,648 B1 10/2001 Doubler et al.
6,306,172 B1 * 10/2001 O'Neil et al. ........... 623/20.15
6,319,286 B1 11/2001 Fernandez et al.
6,355,069 B1 * 3/2002 DeCarlo et al. .......... 623/23.26
6,413,279 B1 * 7/2002 Metzger et al. .......... 623/20.29
6,440,171 B1 8/2002 Doubler et al.
6,475,241 B2 * 11/2002 Pappas .................... 623/20.29
6,485,519 B2 * 11/2002 Meyers et al. ............ 623/20.24
6,491,726 B2 * 12/2002 Pappas .................... 623/20.29
6,589,283 B1 * 7/2003 Metzger et al. .......... 623/20.35
6,616,697 B2 9/2003 Sotereanos
6,620,198 B2 * 9/2003 Burstein et al. .......... 623/20.28
6,660,039 B1 * 12/2003 Evans et al. .............. 623/20.29
6,702,822 B1 3/2004 Noiles et al.
6,702,854 B1 3/2004 Cheal et al.
6,719,800 B2 * 4/2004 Meyers et al. ............ 623/20.24
6,755,864 B1 * 6/2004 Brack et al. .............. 623/20.29
6,773,461 B2 * 8/2004 Meyers et al. ............ 623/20.24
6,866,683 B2 * 3/2005 Gerbec et al. ............ 623/18.11
7,044,975 B2 5/2006 Cheal et al.
2001/0003803 A1 * 6/2001 Leclercq .................. 623/20.29
2001/0034554 A1 * 10/2001 Pappas .................... 623/20.29
2002/0103541 A1 * 8/2002 Meyers et al. ............ 623/20.24
2002/0156535 A1 * 10/2002 Pappas .................... 623/20.29
2003/0009231 A1 * 1/2003 Gundlapalli et al. ..... 623/20.29
2003/0009232 A1 * 1/2003 Metzger et al. .......... 623/20.29
2003/0055508 A1 * 3/2003 Metzger et al. .......... 623/20.15
2003/0153979 A1 * 8/2003 Hughes et al. ........... 623/20.28
2004/0002767 A1 * 1/2004 Wyss ....................... 623/20.27
2004/0054416 A1 * 3/2004 Wyss et al. ............... 623/20.27
2004/0117023 A1 * 6/2004 Gerbec et al. ............ 623/18.11
2004/0162620 A1 * 8/2004 Wyss ....................... 623/20.27
2004/0215345 A1 * 10/2004 Perrone et al. ........... 623/20.32
2004/0249467 A1 * 12/2004 Meyers et al. ............ 623/20.24
2005/0107886 A1 * 5/2005 Crabtree et al. .......... 623/20.24
2005/0192672 A1 * 9/2005 Wyss et al. ............... 623/20.27
2005/0203629 A1 * 9/2005 Cipolletti et al. ......... 623/20.15
2006/0142867 A1 * 6/2006 Metzger et al. .......... 623/20.15

FOREIGN PATENT DOCUMENTS

WO WO00/72784 12/2000
WO WO2005/034817 4/2005

* cited by examiner 19
3
2
C
1

19
3
15
21
2
22
1

3
2
C
1

3
15
2
24
1

MODULAR KNEE PROSTHESIS

INCORPORATIONS BY REFERENCE

The present application claims benefit of provisional application No. 60/547,627, which is incorporated by reference herein in its entirety.

BACKGROUND OF THE INVENTION

1. Field of the Invention

The present disclosure relates generally to an implantable article that is particularly suitable for use as an artificial joint prosthesis and more particularly to a prosthesis shaving in part a tray that is supported by metaphyseal bone, such as the tibial component of a knee prosthesis.

2. Description of the Related Art

Artificial knee joint prostheses are widely used today, restoring mobility to patients affected by a variety of conditions, particularly arthritis. The satisfactory performance of these devices can be affected not only by the design of the prosthesis itself, but also by the final placement and spatial orientation of the implanted components both individually and together in combination. Improper placement or orientation of one or more components of the device or an improper fit to the patient's anatomy can adversely affect the goal of satisfactorily restoring the clinical biomechanics and function of the joint.

There are several general types of total knee joint replacement prostheses, including fixed bearing, mobile bearing, and rotating platform, in both hinged and semi-constrained designs. The primary difference between the fixed bearing designs and the mobile bearing and rotating platform designs is that the mobile bearing and rotating platform designs uncouple, to some degree, the motion of the tibial tray from the motion of the component that articulates with the femoral component. In a typical rotating platform design, for instance, the plastic articular component is free to rotate about an axis that is roughly parallel to the long axis of the tibia, while the tibial tray remains stationary relative to the tibia.

The positioning of the device, including the rotational alignment of the tibial component relative to the femoral component, affects the biomechanics of the joint. The proper rotational alignment of the tray on the tibia allows for greater coverage of the metaphyseal bone with more complete bony support of the tray and little or no overhang. The proper rotational alignment of the tibial articular surface with the femoral articular surface allows these components to articulate in the manner for which they were designed, and in this way maximizes the contact area between the articular surfaces, minimizes the contact stresses for a given flexion angle and joint load, and thus minimizes wear of the articular surfaces. While rotating platform and mobile bearing designs can provide this de-coupling of the tibial tray and articular surface alignments, these designs employ an additional articulation between the plastic tibial articular component and the supporting metal tray that is a potential source for material wear. It is therefore desirable to provide a component that de-couples the rotational alignment of the tray to the proximal tibia from the alignment of the tibial bearing component to the femoral component, thus allowing for both optimal articulation and secure engagement to be achieved, independent of each other, without the additional metal-to-plastic articulation that is incumbent to mobile bearing and rotating platform designs.

SUMMARY OF THE INVENTION

It is an aspect of the present general inventive concept to provide a component designed to allow for tibial component articular surface rotational alignment that can be set independent of the rotational position of the tibial portion that is in direct contact with the tibia.

The above aspects can be attained by a joint prosthesis that includes (a) a tibial tray member so sized and shaped as to replace the proximal end of the tibia, and having (b) a bore with internal size and shape so as to receive the coupler member; (c) a tibial base member, having (d) a distal surface so shaped as to interface with the proximal surface of the tibial tray member; (e) a proximal geometry so shaped as to attach to the tibial articular member; and (f) a bore with internal size and shape so as to receive the coupler member; (g) a tibial articular member, having (h) a proximal surface so sized and shaped as to articulate with the femoral member; (i) a distal surface so sized and shaped as to attach to the tibial base member; and (j) an opening or other mechanism by which assembly of the coupler member to the tibial base member and tibial tray member is enabled; (k) a coupler member, having (l) a distal mating portion so sized and shaped as to be received inside the bore in the tibial tray member, (m) a proximal mating portion so sized and shaped as to be received inside the bore in the tibial base member; (n) a femoral member so sized and shaped as to replace the distal end of the femur, and having an outer surface so sized and shaped as to articulate with the tibial articular member.

These together with other aspects and advantages which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

Further features and advantages of the present inventive concept, as well as the structure and operation of various embodiments of the present inventive concept, will become apparent and more readily appreciated from the following description of the preferred embodiments, taken in conjunction with the accompanying drawings of which.

DESCRIPTION OF THE PREFERRED EMBODIMENTS

Figure 1:
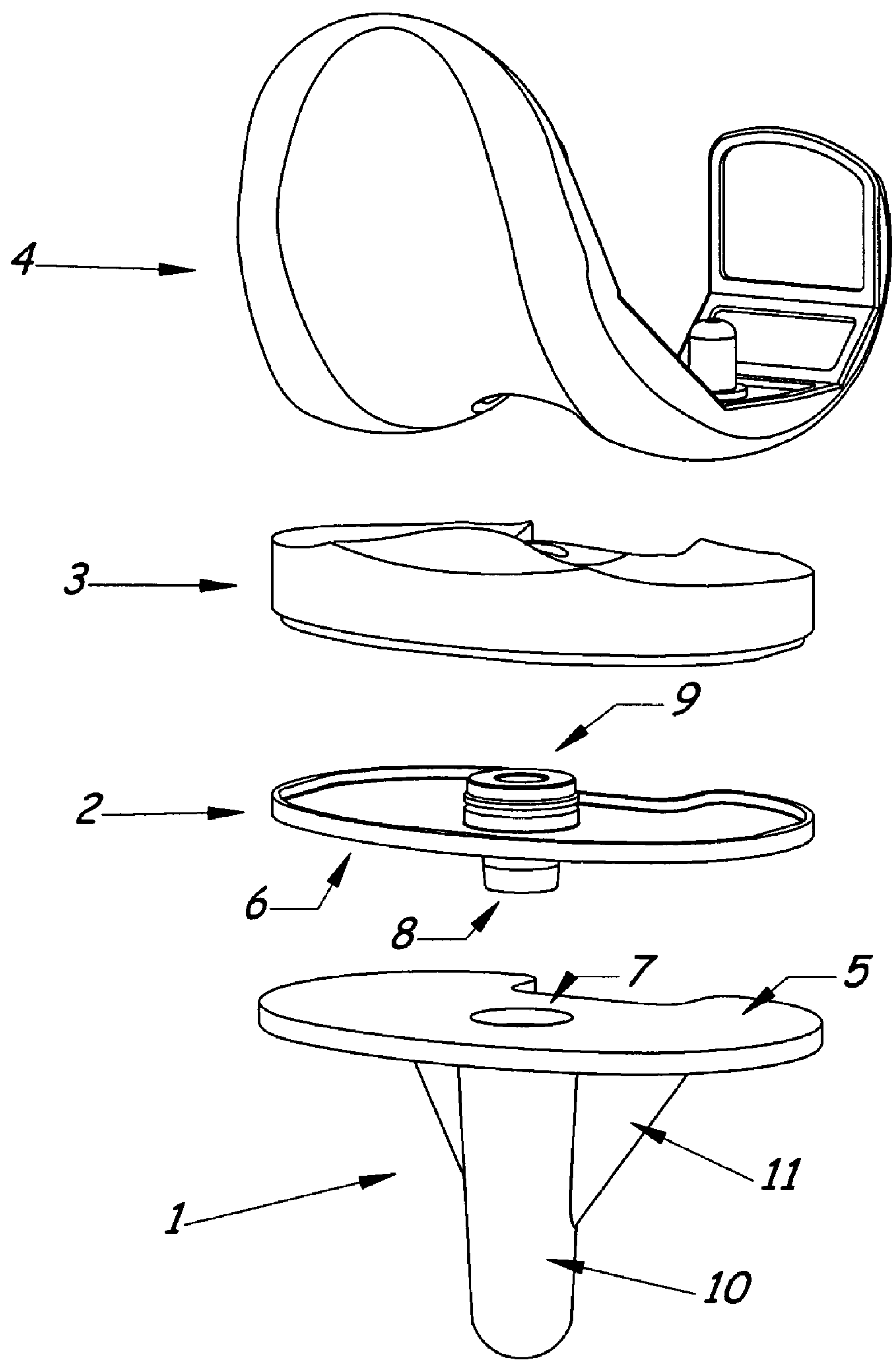
FIG. 1 is an exploded view of the prosthetic device of the present inventive concept.

Reference will now be made in detail to the presently preferred embodiments of the inventive concept, examples of which are illustrated in the accompanying drawings, wherein like reference numerals refer to like elements throughout.

The present inventive concept is related to the tibial component of a knee replacement prosthesis for both cemented and cementless applications; however the inventive concept is also applicable to other implantable prostheses such as ankles, fingers, and elbows, all of which may include a tray portion for resurfacing one or both sides of a joint. The present inventive concept is particularly advantageous in allowing optimal sizing and placement for use in an artificial knee and as such this description will reference a knee prosthesis.

The components that comprise these devices are designed such that assembly of the components can be accomplished either before implantation, such as on the back table during surgery, or, alternatively the assembly can be accomplished in a successive fashion, assembling each portion independently during implantation to maximize the benefits of independent positioning of the individual sub-components of the device in the joint. The tibial component articular portion can be fixedly set in place, or it can be left free to rotate after implantation, employing metal-on-metal bearing surfaces for the rotational motion.

The present inventive concept can be achieved by de-coupling the tibial tray and tibial bearing portions, resulting in two or more distinct pieces. The tibial articular portion articulates with the femoral portion that is in direct contact with the femur to provide functional replacement of the knee joint. The tibial base portion supports this tibial articular portion, and the tibial tray portion in turn supports the tibial base portion. The tibial tray portion is in direct contact with the proximal tibia. The tibial articular portion and tibial base portion may be preassembled during manufacture or may be removably attached by the user (surgeon), forming the tibial bearing portion. The user, to allow rotational alignment of the articular portion independent from and relative to the tray portion, may combine the tibial bearing portion with the tibial tray portion. This achieves additional variable positioning independent of that achieved after insertion of the tray portion. In one embodiment, the tibial bearing portion can be locked to the tray portion within a range of rotational positions to achieve the desired rotational alignment with the femoral component. In another embodiment, the tibial bearing portion is free to rotate on the tibial tray portion after assembly. By varying bearing portion configurations a variety of clinical needs and situations can be addressed, such as adding thickness to the bearing portion for proper soft tissue tensioning. Sizes of the tray portion and the femoral portion can also be independently selected, for proper fitment to the tibia and femur respectively, while maintaining a size match between the tibial articular portion and the femoral portion. Many different clinical situations can be addressed by simply using the appropriate combination of tibial tray, base, and articular portions, and femoral portions.

A cylindrical press-fit coupling mechanism between the tibial base portion and the tibial tray portion provides a reproducible strength and geometry of assembly between the two portions; this coupling mechanism only requires axial translation of the coupling mechanism, where full assembly is defined by seating of the base portion to the tray portion, which could not be achieved with the use of a tapered coupling mechanism. The coupling mechanism itself is either integral to the base portion or is accomplished with a separate portion that couples to the base and tray portions. Provided the coupling mechanism is fully assembled, the resulting strength of assembly and the axial position of the base portion relative to the tray portion are dependent on the design and manufacturing tolerances, and are not dependent on the magnitude of force applied during assembly, unlike tapered and/or threaded coupling mechanism.

Due to the extent of options available, and the desire for a system approach in addressing a multitude of clinical situations with limited components, a connection mechanism between the components is simplified and common amongst the components resulting in a reliable, more cost effective, and user friendly mechanism to secure the components either prior to, immediately prior to, or during implantation.

Figure 2:
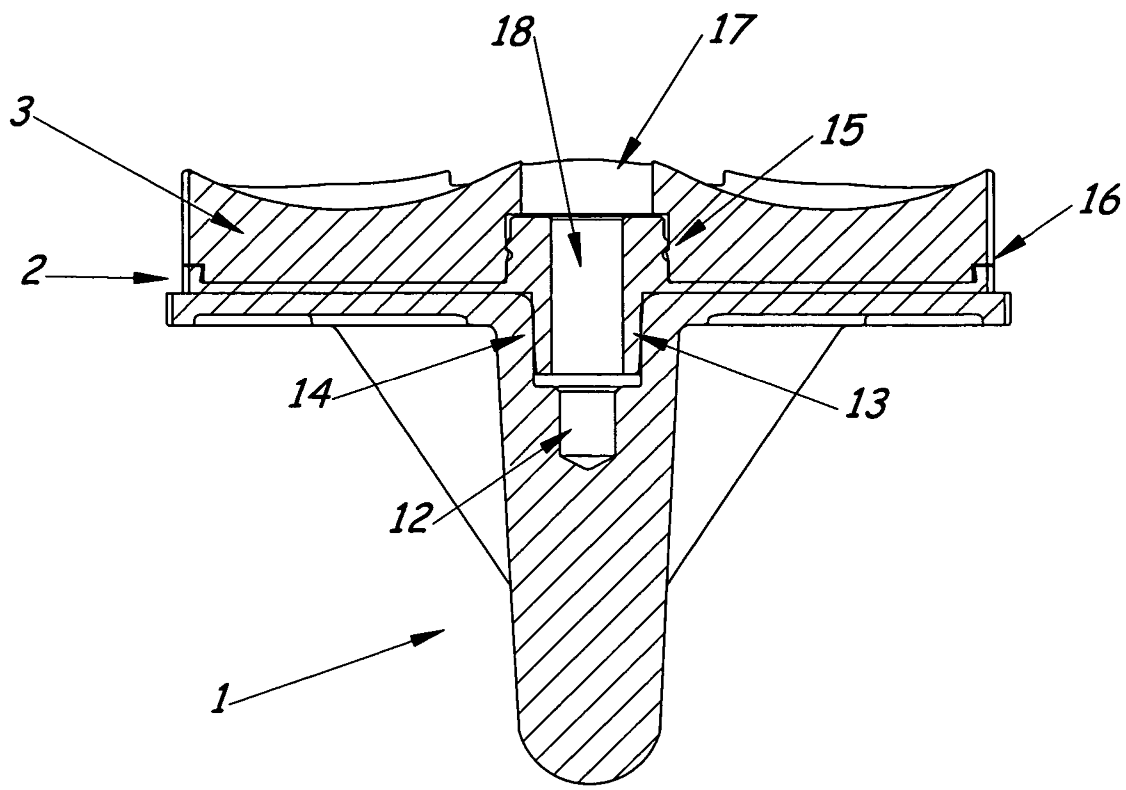
FIG. 2 is a section view through part of the prosthetic device of the present inventive concept.

As shown in FIG. 1 there is a tray portion (1) of the device that is the portion that interfaces to the proximal end of the tibia. The tray portion (1) is independent from the tibial base portion (2), the two portions being assembled and joined by the attachment mechanism shown in FIG. 2. The tibial articular portion (3) fixedly attaches to the base portion (2), together forming the tibial bearing portion. The tibial articular portion (3) articulates with the femoral portion (4) to complete a functional knee replacement. Optionally, the knee replacement may include a patellar portion (not shown), for resurfacing or replacing the patella, that articulates with the femoral portion. The assembly of the device is not limited temporally, in that assembly can occur before surgery, immediately prior to implantation, or during implantation.

The distal portion of the tibial tray may include one or more stems (10), ribs (11), pegs or other geometric or surface features for stabilization in the tibia. Centrally located on the proximal end of the tray is a bore (7) with a central axis that is oriented normal to the proximal surface (5) of the tray. The bore (7) may include threads or other feature (12) for engaging a screw, bolt, rod, or similar, which may be removably engaged to the tray portion (1). Such rod, or similar, may be used as part of an assembly device, to apply an assembly force to the tray while such device applies an opposite force to the bearing portion, to forcibly assemble the bearing portion into the tray. The bore (7) may also serve as a mechanism of removing the tray from the bone in which the tray is implanted using a suitable instrument that removably engages the tray.

The base portion (2) is independent of the tray portion (1) and assembled and joined to the tray portion by the user (typically the surgeon). This modular feature is what allows the user additional flexibility in final knee replacement configuration. By de-coupling tray placement from the articular surface orientation, substantially more flexibility is allowed and the ability to address internal or external rotational malalignment becomes available. In addition, optimal sizing (including thickness, width, and breadth) may be achieved by choosing the appropriate articular and base portions to use with the chosen tray portion. The base portion (2) includes a male spigot (8) that inserts in a co-axial manner into the bore (7) in the tray portion (1). The proximal surface (5) of the tray portion and the distal surface (6) of the base portion have mutually conforming surfaces that come into direct contact upon assembly of the base portion to the tray portion.

Final locking of the base portion (2) to the tray portion (1) is obtained by the male spigot (8) of the base portion (2) locking within the corresponding bore (7) of the tray portion (1). One or more zones of diametrical interference between the spigot (8) and bore (7) achieve this locking. In the zone of diametrical interference on the spigot (13) and the corresponding zone of diametrical interference on the bore (14), the engaging surfaces of the spigot and bore are cylindrical. To obtain the interference fit between the spigot and bore at these zones (13 and 14), the outside diameter of the spigot exceeds the inside diameter of the bore, which defines the diametrical interference. The diametrical interference between the spigot and the bore is critical to proper functioning of the device, and may be in the range of 0.0005" to 0.0035". The preferred embodiment utilizes a nominal diametrical interference of 0.0020". The length of the zone of diametrical interference may be limited to approximately 0.02" to 0.10" to provide adequate rotational resistance of the base portion within the tray portion, while maintaining reasonable assembly forces by controlling the amount of interference, the length of the zone and the axial location of the zone(s). In the preferred embodiment, both the spigot (8) and bore (7) incorporate gradual tapers and/or rounds at the surfaces leading into the zones of diametrical interference so as to avoid plowing of one or more surfaces during assembly, and thus ease assembly of the base portion to the tray portion. The total length of the spigot (8) and the location of the cylindrical zone with diametrical interference (13 and 14 of the spigot and bore, respectively) is not critical, it only requires a length and location to ensure a suitable locking surface with adequate axial and torsional engagement. It has been determined that an axial length of diametrical interference of approximately 0.08" and a total length of the spigot (8) of 0.3" are satisfactory for the tibial component of a knee replacement.

The tibial articular portion (3) and tibial base portion (2) may be distinct modular components that are assembled by the user prior to implantation, or assembled by the user during implantation. One or more of a variety of a locking mechanism (15 and 16) may be utilized to fixedly combine the articular portion and the base portion. Alternatively assembly of the two portions into a single portion may effectively combine these two portions into a single portion during manufacture, or by replacing the two portions with a single portion that provides the same functionality as the two portions in combination. The tibial articular portion and tibial base portion together comprise the tibial bearing portion.

The tibial base portion (2) and tibial articular portion (3) may include through holes (17 and 18) coaxial to the spigot (8). These through holes (17 and 18) may include threads or other mechanisms for removable engagement of a bolt, rod, or plug, together or separately and for various purposes. A bolt or rod could provide a mechanism of removing the base portion from the tray portion, or removing the assembled construct from the bone. A plug could be used to close the hole and keep the internal surfaces clean. The through holes (17 and 18) could also be used to enable a rod to pass through the base portion (2) and articular portion (3), said rod removably engaging the tray portion (1) at the hole (12), as part of a device to forcibly assemble the base portion into the tray portion. Alternatively, a bolt or other fastener could further secure the tibial bearing portion to the tray portion.

Figure 4:
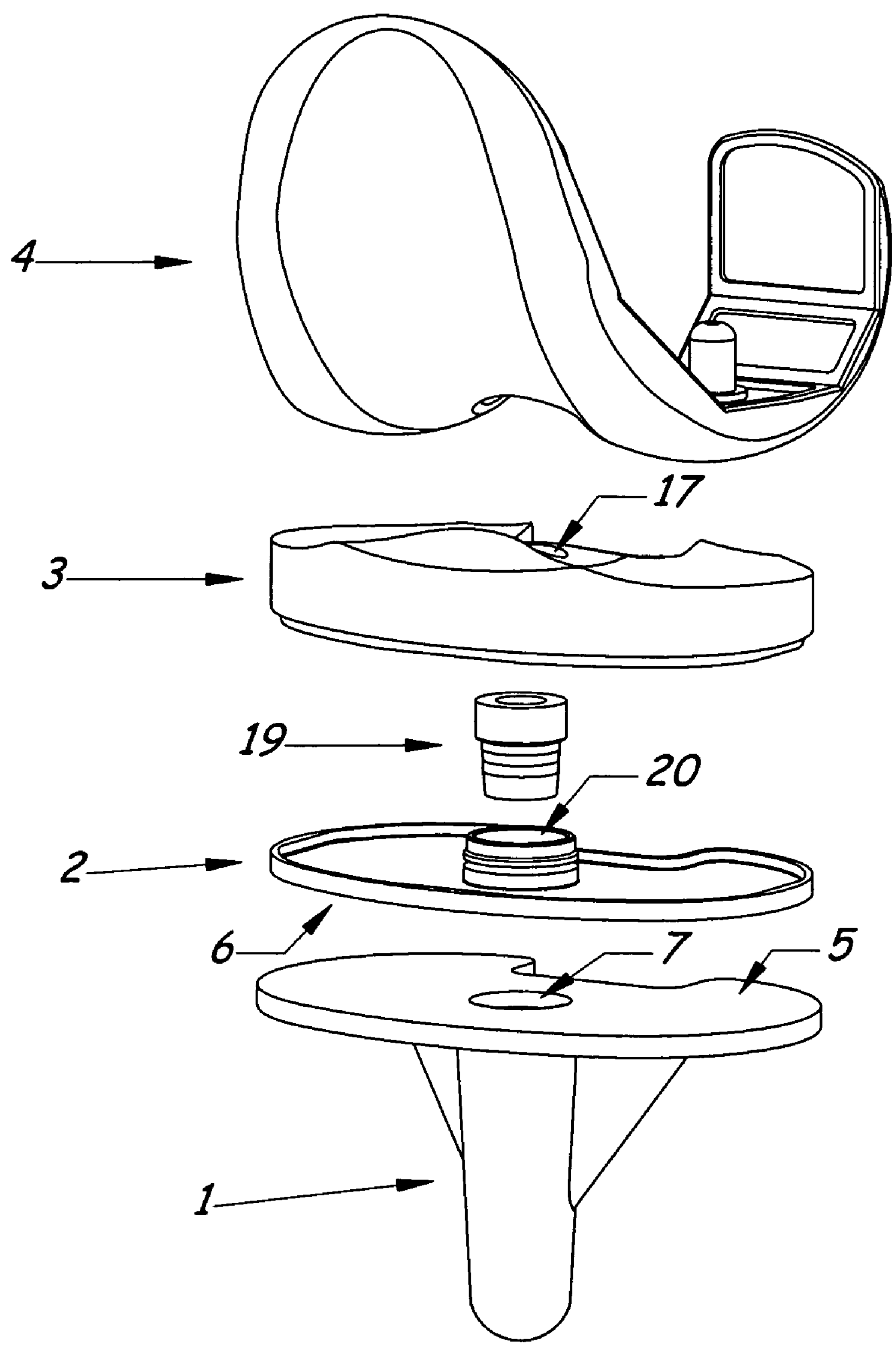
FIG. 4 is an exploded view of another embodiment of the prosthetic device of the present inventive concept.
Figure 5:
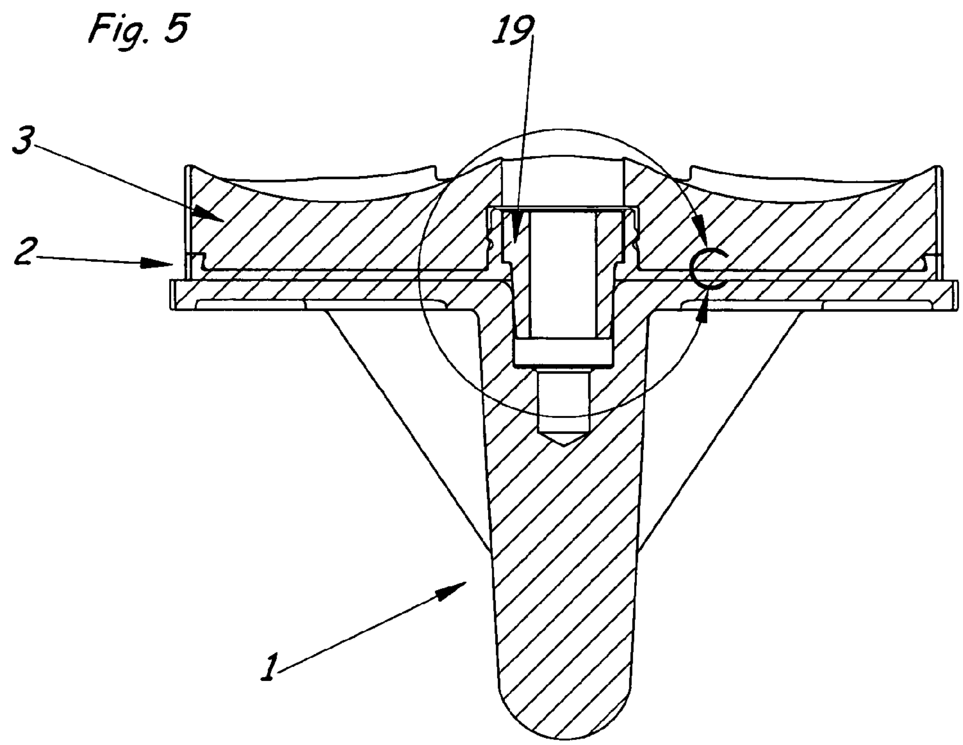
FIG. 5 is a section view through part of the embodiment depicted in FIG. 4.
Figure 6:
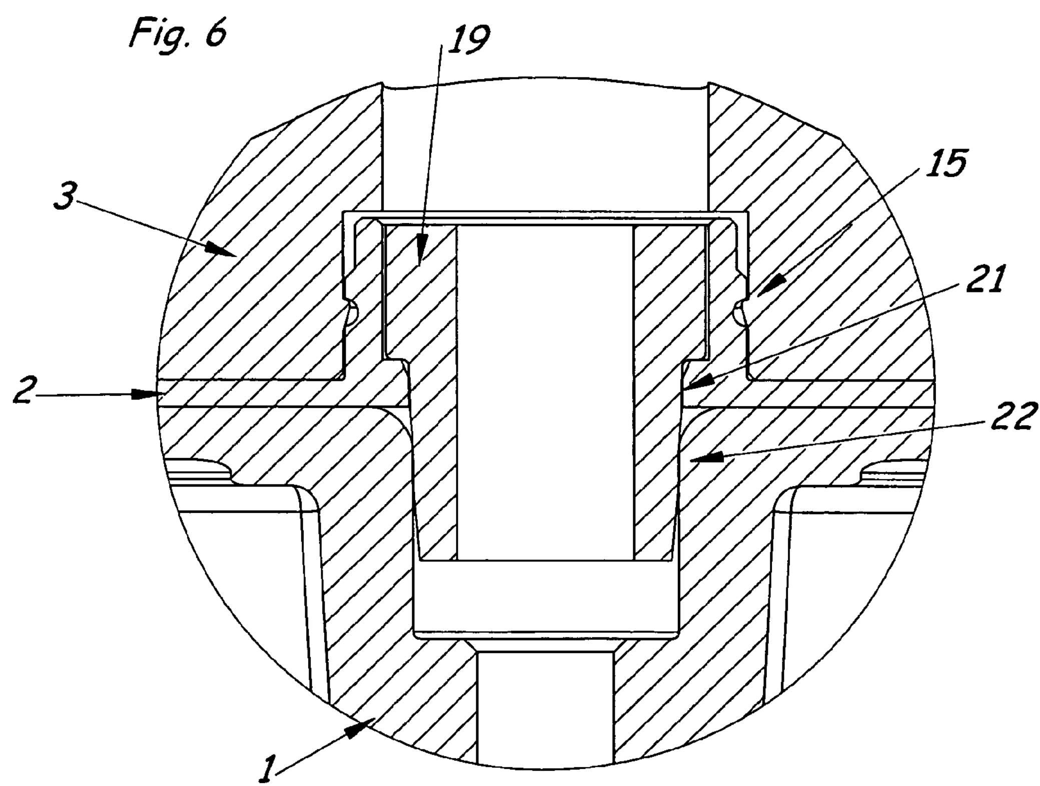
FIG. 6 is a detailed view of FIG. 5, with the area of detail indicated by the circle (C) in FIG. 5.

In another embodiment of the present inventive concept, shown in FIGS. 4-6, a coupler portion (19) is used to achieve the cylindrical press-fit engagement of the base portion (2) to the tray portion (1). In this embodiment, the function of the spigot (8) on the base portion is replaced by the coupler portion (19). The coupler portion includes two zones of diametrical interference, one of which engages the tibial base (21) and the other of which engages the bore in the tray (22). To assemble the components, the coupler portion (19) is inserted through the hole in the base (20), until the coupler engages the base and the tray at these zones of diametrical interference, and fully seats the distal surface of the base (6) against the proximal surface of the tray (5). In the zones of diametrical interference, the engaging surfaces of the coupler, base, and bore are cylindrical. To obtain the interference fit between the coupler and the base, and between the coupler and the bore, at these proximal (coupler-base) and distal (coupler-tray) zones of interference (21 and 22, respectively), the outside diameter of the coupler exceeds the inside diameter of the base and the inside diameter of the bore. To ease assembly, the diameter of the coupler at the distal zone of interference (22) may be smaller than the diameter of the base at the proximal zone of interference (21). The diametrical interference between the coupler and the base at the proximal zone (22), and between the coupler and the bore at the distal zone (21), are critical to proper functioning of the device, and may each be in the range of 0.0005" to 0.0035". The preferred embodiment utilizes a nominal diametrical interference of 0.0020" at each of the two zones of interference fit (21 and 22). The length of the zones of diametrical interference may be limited to approximately 0.02" to 0.10" to provide adequate rotational resistance of the base portion within the tray portion, while maintaining reasonable assembly forces by controlling the amount of interference, the length of the zones and the axial location of the zones. In the preferred embodiment, the coupler (19), base (2), and bore (7) incorporate gradual tapers and/or rounds at the surfaces leading into the zones of diametrical interference so as to avoid plowing of one or more surfaces during assembly, and thus ease assembly of the coupler portion to the base and tray portions. The total length of the coupler (19) and the location of the cylindrical zones with diametrical interference (21 and 22) are not critical, they only require length and locations to ensure suitable locking surfaces and adequate axial and torsional engagement. It has been determined that a length of engagement of diametrical interference of approximately 0.08" between the coupler and the bore (22) and a length of engagement of diametrical interference of approximately 0.02" between the coupler and the base (21) are satisfactory for the tibial component of a knee replacement.

Figure 7:
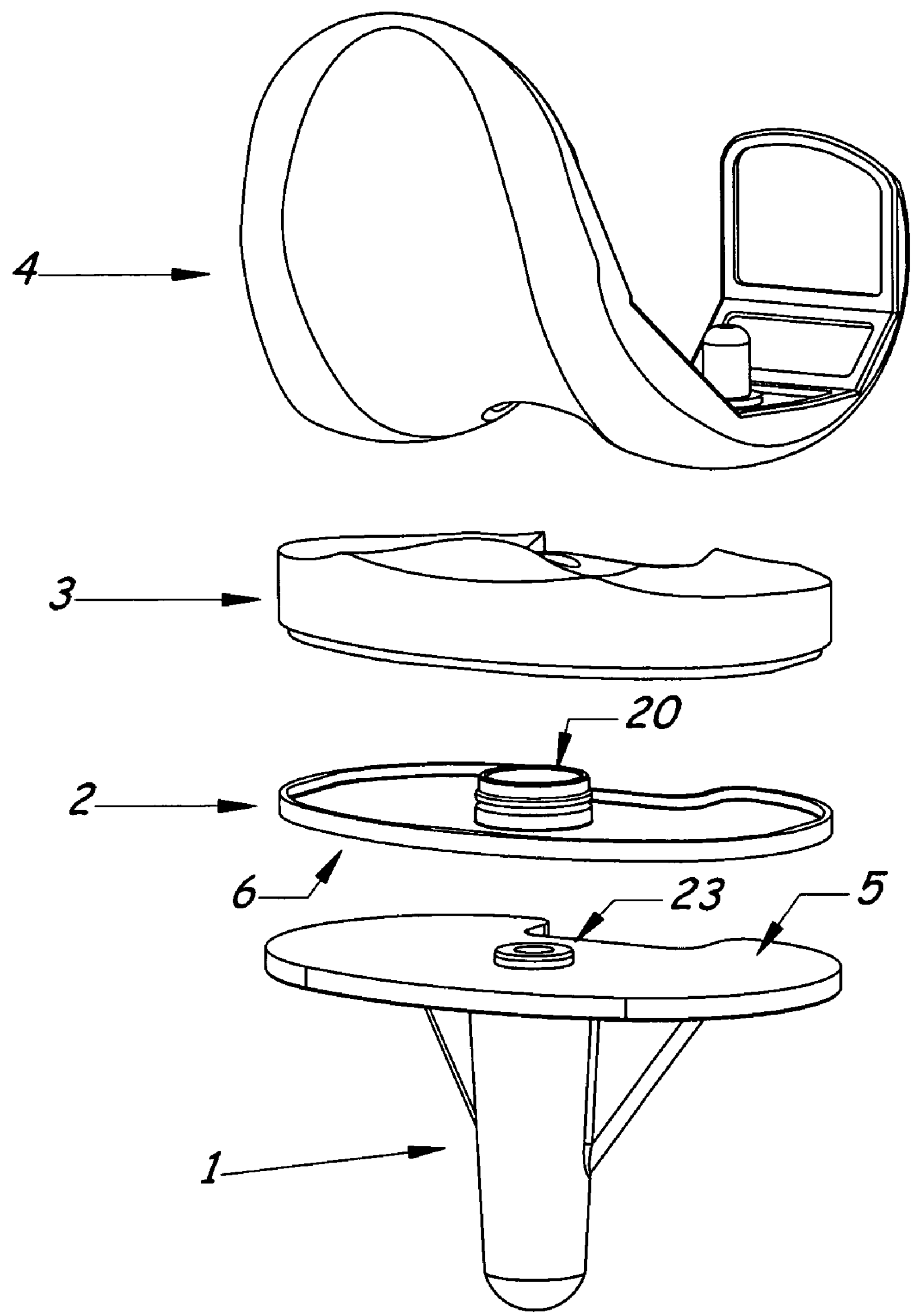
FIG. 7 is an exploded view of another embodiment of the prosthetic device of the present inventive concept.
Figure 8:
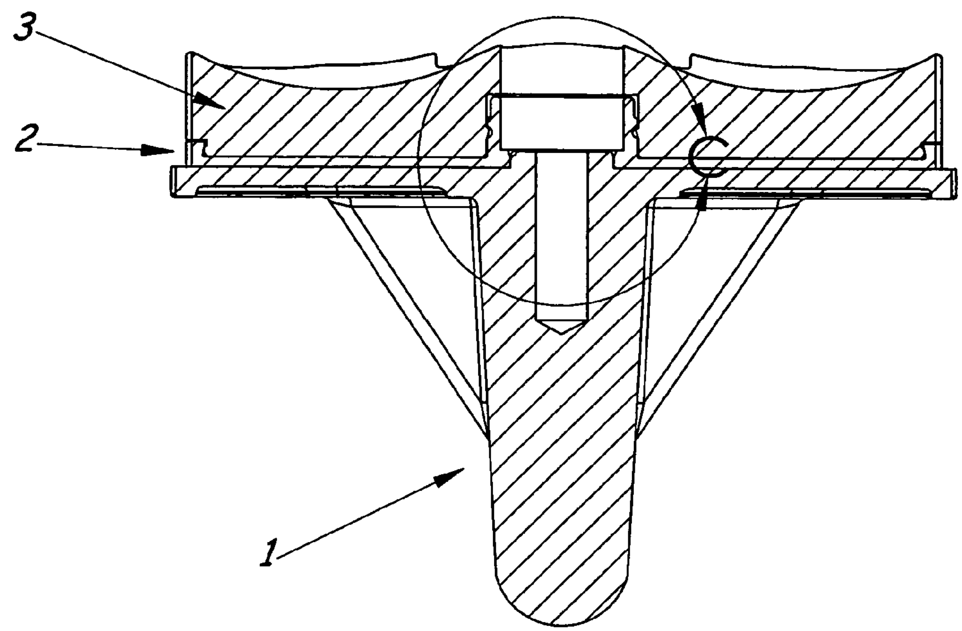
FIG. 8 is a section view through part of the embodiment depicted in FIG. 7.
Figure 9:
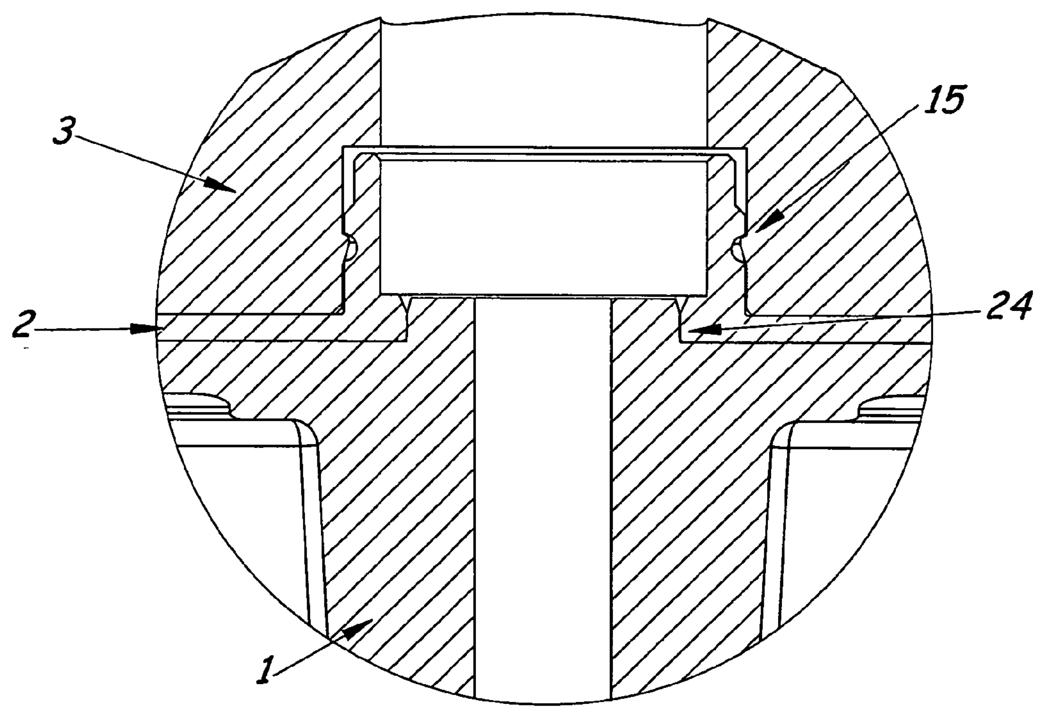
FIG. 9 is a detailed view of FIG. 8, with the area of detail indicated by the circle (C) in FIG. 8.

In another embodiment of the present inventive concept, shown in FIGS. 7-9, the male spigot (23) is part of the tibial tray (1), and this spigot engages the bore (20) in the base to achieve the cylindrical press-fit engagement of the base portion (2) to the tray portion (1). The spigot (23) includes at least on zone of diametrical interference (24), which engages the tibial base (2). To assemble the components, the base portion (2) is placed on top of the tray portion (1), with the spigot (23) inserted in the hole in the base (20), engaging the spigot with the base at the zone of diametrical interference (24), and pressing the base portion onto the tray portion until the distal surface of the base (6) is fully seated against the proximal surface of the tray (5). In the zone of diametrical interference on the spigot and bore (24), the engaging surfaces of the spigot and bore are cylindrical. To obtain the interference fit between the spigot and the bore, the outside diameter of the spigot exceeds the inside diameter of the bore. The diametrical interference between the spigot and the bore is critical to proper functioning of the device, and may each be in the range of 0.0005" to 0.0035". The preferred embodiment utilizes a nominal diametrical interference of 0.0020" at the zone of interference fit (24). The length of the zone of diametrical interference may be limited to approximately 0.02" to 0.10" to provide adequate rotational resistance of the base portion on the tray portion, while maintaining reasonable assembly forces by controlling the amount of interference, the length of the zone and the axial location of the zone. In the preferred embodiment, the spigot (23) and bore (20) incorporate gradual tapers and/or rounds at the surfaces leading into the zones of diametrical interference so as to avoid plowing of one or more surfaces during assembly, and thus ease assembly of the base and tray portions. The total length of the spigot (23) and the location of the cylindrical zone with diametrical interference (24) are not critical, they only require a length and location to ensure suitable locking surfaces and adequate axial and torsional engagement. It has been determined that a length of engagement of diametrical interference of approximately 0.06" between the spigot and the bore (24) is satisfactory for the tibial component of a knee replacement.

Figure 3:
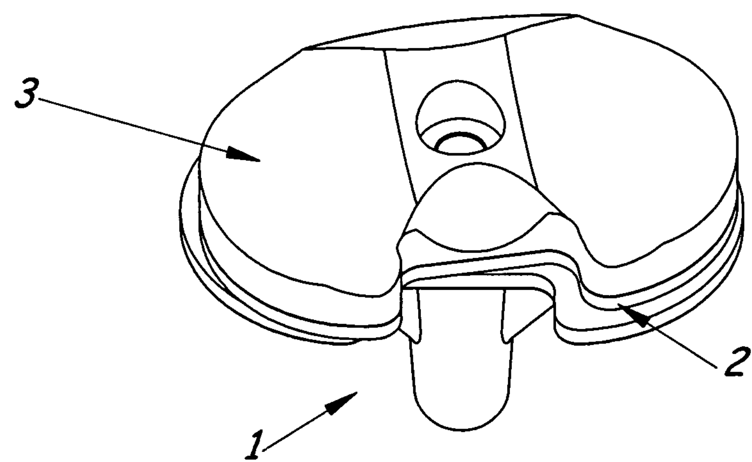
FIG. 3 shows the prosthetic device of the present inventive concept with the bearing portion (articular and base portions) in one of many possible assembled positions, in this case rotated 10 degrees relative to the tray portion.

In another embodiment of the present inventive concept, a slip-fit engagement, with line-to-line fit or a small diametrical clearance in place of the diametrical interference, allows rotational motion of the tibial base portion (2) relative to the tibial tray portion (1) after assembly and during functional service. In the embodiment shown in FIGS. 1-3, this slip-fit engagement is between the spigot (8) and the bore (7). In the embodiment shown in FIGS. 4-6, this slip-fit engagement is between the coupler (19) and the bore in the base portion (20), or alternatively between the coupler (19) and the bore in the tray portion (7). In the embodiment shown in FIGS. 7-9, this slip-fit engagement is between the spigot (23) and the bore (20). In each of these embodiments with slip-fit engagement, the tibial base portion (2) and the fixedly attached tibial articular portion (3) can, as a unit, rotate about the axis of the cylindrical bore (7 or 20). This rotational freedom allows the tibial articular surface to remain in continuous alignment with the femoral component after implantation, with metal-on-metal bearing rather than the metal-on-plastic bearing of previous rotating platform or mobile bearing designs.

The modular tibial base portion (2) and tibial articular portion (3) allow one to utilize various bearing configurations with the same tray portion (1) allowing for multiple options for each and every tray. Variations of articular portions (3) can include but not limited to different thickness articular portions, alternative materials or material processing, and various articular geometries. Articular geometries may include additional features for engaging the femoral component, such as a post as part of a posterior stabilized design. The coupler portion (19), as an additional function, may form all or part of such a feature. When variations of femoral and/or patellar portions are included the design options multiply significantly with very little increase in number of individual subcomponents. Femoral component options may include, but are not limited to, well known unconstrained, semi-constrained, posterior stabilized, and hinged designs, with appropriate mating tibial articular portions.

The tibial tray (1), base (2), and articular (3) portions, and the femoral (4) and patellar portions of this device, can be fabricated from any suitable high strength biocompatible materials. Suitable materials include any of the titanium alloys, cobalt alloys, or stainless steel alloys. Preferred examples include cobalt chromium alloys for the tibial tray and base portions, and for the femoral portion, and ultrahigh molecular weight polyethylene for the tibial articular portion and the patellar portion. The polyethylene articular portion can be machined from prefabricated stock material, or it can be compression molded from polyethylene powder as a separate unit, and assembled to the tibial base during manufacturer or by the user. Alternatively, the polyethylene can be directly compression molded into the tibial base portion forming an integral unit at the time of manufacturer. The distal geometry and surface properties of the tray portion can be any of a variety appropriate for interfacing with the recipient bone for cemented or cementless fixation. The geometry and surface properties of the femoral portion (4) on the generally concave surface can be any of a variety appropriate for interfacing with the recipient bone for cemented or cementless fixation.

Although the present inventive concept and its advantages have been described in detail, it should be understood that various changes, substitutions and alterations can be made herein without departing from the spirit and scope of the inventive concept as defined by the appended claims. This could include such changes so as to apply the inventive concept to other joints besides the knee joint.

What is claimed is:

1. A joint prosthesis comprising a tibial tray, a tibial base, a coupler, a tibial articular member, and a femoral articular member, wherein:

the tibial tray, the tibial base, the coupler and the tibial articular member define a common axis;

the tibial tray comprises a stem protruding distally from a proximal surface, the proximal surface:

sized and shaped to cover at least part of a cut proximal end of a tibia; and defining a bore therethrough;

the tibial base comprises:

a distal surface sized and shaped to interface with the proximal surface of the tibial tray; and a proximal surface sized and shaped to attach to the tibial articular member;

the coupler comprises:

a proximal portion that contacts the tibial base, holds the distal surface of the tibial base in contact with the proximal surface of the tibial tray, and permits rotation of the tibial base about the common axis with respect to the tibial tray; and a distal portion that is received in the tibial tray bore with a diametrical interference fit;

the tibial articular member comprises:

a distal surface so sized and shaped as to attach to the proximal surface of the tibial base and to permit the tibial articular member to rotate about the common axis with the tibial base; and a proximal surface sized and shaped to articulate with the femoral articular member; and the femoral articular member comprises:

a distal surface sized and shaped to articulate with the proximal surface of the tibial articular member; and a proximal surface sized and shaped to replace at least part of a cut proximal end of a femur.

2. The joint prosthesis of claim 1, wherein the coupler comprises a shoulder that so engages a lip on the tibial base as to prevent disassociation of the tibial base from the tibial tray.

3. The joint prosthesis of claim 1, wherein the tibial tray stem, the tibial base, and the tibial articulating member each defines a bore aligned with the tibial tray proximal surface bore.

4. The joint prosthesis of claim 1, wherein the distal portion of the coupler that participates in the interference fit with the tibial tray bore has a constant cross-sectional geometry along its length.

5. The joint prosthesis of claim 4, wherein the distal portion of the coupler that participates in the interference fit with the tibial tray bore is cylindrical or substantially cylindrical along its length.

6. The joint prosthesis of claim 5, wherein the distal portion of the coupler that participates in the interference fit with the tibial tray bore is cylindrical along its length.

7. The joint prosthesis of claim 1, wherein the interference fit is an interference press-fit.

8. The joint prosthesis of claim 1, wherein the tibial tray comprises metal, and the tibial base comprises metal.

9. A joint prosthesis comprising a tibial tray, a tibial base, a tibial articular member, and a femoral articular member, wherein:

the tibial tray comprises a proximal surface and a stem protruding distally from the proximal surface, the proximal surface being sized and shaped such that when the stem is seated in a medullary canal of a tibia from which a proximal portion has been removed, the proximal surface would cover at least part of a cut proximal end of the tibia;

the tibial base comprises:

a distal portion having a mating surface with a constant non tapering cross-sectional geometry along its length that engages the tibial tray with an interference press-fit; and a proximal surface sized and shaped to attach to the tibial articular member;

the tibial articular member comprises a single piece that includes:

a distal surface so sized and shaped as to attach to the proximal surface of the tibial base; and a proximal surface sized and shaped to articulate with the femoral articular member; and the femoral articular member comprises:

a distal surface sized and shaped to articulate with the proximal surface of the tibial articular member; and a proximal surface sized and shaped to replace at least part of a cut proximal end of a femur.

10. The joint prosthesis of claim 9, wherein the proximal surface of the tibial tray defines a bore, and the distal portion of the tibial base comprises a protrusion that is received in the tibial tray bore to form the interference press-fit.

11. The joint prosthesis of claim 9, wherein the distal portion of the tibial base defines a bore, and the proximal surface of the tibial tray comprises a protrusion that is received in the tibial base bore to form the interference press-fit.

12. A joint prosthesis comprising a tibial tray, a tibial base, a coupler, a tibial articular member, and a femoral articular member, wherein:

the tibial tray comprises a proximal surface and a stem protruding distally from the proximal surface, the proximal surface defining a bore therethrough, the proximal surface being sized and shaped such that when the stem is seated in a medullary canal of a tibia from which a proximal portion has been removed, the proximal surface would cover at least part of a cut proximal end of the tibia;

the tibial base comprises:

a distal surface sized and shaped to interface with the proximal surface of the tibial tray; and a proximal surface sized and shaped to attach to the tibial articular member;

the coupler comprises:

a proximal portion that engages the tibial base with a diametrical interference fit; and a distal portion that engages the tibial tray bore with a diametrical interference fit;

the tibial articular member comprises:

a distal surface so sized and shaped as to attach to the proximal surface of the tibial base; and a proximal surface sized and shaped to articulate with the femoral articular member; and the femoral articular member comprises:

a distal surface sized and shaped to articulate with the proximal surface of the tibial articular member; and a proximal surface sized and shaped to replace at least part of a cut proximal end of a femur.

13. The joint prosthesis of claim 12, wherein the coupler comprises a shoulder that engages a lip on the tibial base to hold the distal surface of the tibial base to the proximal surface of the tibial tray.

14. The joint prosthesis of claim 12, wherein the tibial tray stem, the tibial base, and the tibial articulating member each defines a bore aligned with the tibial tray proximal surface bore.

15. The joint prosthesis of claim 12, wherein the distal portion of the coupler that participates in the interference fit with the tibial tray has a constant cross-sectional geometry.

16. The joint prosthesis of claim 15, wherein the distal portion of the coupler that participates in the interference fit with the tibial tray is cylindrical or substantially cylindrical.

17. The joint prosthesis of claim 16, wherein the distal portion of the coupler that participates in the interference fit with the tibial tray bore is cylindrical.

18. The joint prosthesis of claim 12, wherein the proximal portion of the coupler that participates in the interference fit with the tibial base has a constant cross-sectional geometry.

19. The joint prosthesis of claim 18, wherein the proximal portion of the coupler that participates in the interference fit with the tibial base is cylindrical or substantially cylindrical.

20. The joint prosthesis of claim 19, wherein the proximal portion of the coupler that participates in the interference fit with the tibial base bore is cylindrical.

21. The joint prosthesis of claim 20, wherein the distal portion of the coupler that participates in the interference fit with the tibial tray bore is cylindrical.

22. The joint prosthesis of claim 18, wherein the distal portion of the coupler that participates in the interference fit with the tibial tray has a constant cross-sectional geometry.

23. The joint prosthesis of claim 12, wherein the interference fits are interference press-fits.

24. The joint prosthesis of claim 12, wherein the tibial tray comprises metal, and the tibial base comprises metal.

* * * * *

UNITED STATES PATENT AND TRADEMARK OFFICE

CERTIFICATE OF CORRECTION

PATENT NO. : 7,753,960 B2
APPLICATION NO. : 11/066123
DATED : July 13, 2010
INVENTOR(S) : George Cipolletti et al.

It is certified that error appears in the above-identified patent and that said Letters Patent is hereby corrected as shown below:

Col. 1, line 15: replace the word “shaving” with --having--.

Signed and Sealed this

Fifth Day of October, 2010

David J. Kappos
*Director of the United States Patent and Trademark Office*